(12) United States Patent
Ehrnsperger et al.

(10) Patent No.: US 8,791,320 B2
(45) Date of Patent: Jul. 29, 2014

(54) ABSORBENT STRUCTURES COMPRISING COATED SUPER-ABSORBENT POLYMER PARTICLES

(75) Inventors: Bruno Johannes Ehrnsperger, Mason, OH (US); Heike Opper, Bad Soden (DE); Udo Friedel Schoenborn, Bad Soden (DE)

(73) Assignee: The Procter & Gamble Company, Cincinnati, OH (US)

( * ) Notice: Subject to any disclaimer, the term of this patent is extended or adjusted under 35 U.S.C. 154(b) by 578 days.

(21) Appl. No.: 11/936,859

(22) Filed: Nov. 8, 2007

(65) Prior Publication Data

US 2008/0103466 A1    May 1, 2008

Related U.S. Application Data

(60) Continuation of application No. 11/474,857, filed on Jun. 26, 2006, now Pat. No. 7,311,968, which is a division of application No. 10/881,090, filed on Jun. 30, 2004, now Pat. No. 7,108,916.

(30) Foreign Application Priority Data

Jun. 30, 2003 (EP) ..................................... 03014926

(51) Int. Cl.
 *A61F 13/15* (2006.01)
(52) U.S. Cl.
 USPC .......................................... 604/368; 604/372
(58) Field of Classification Search
 USPC ................................................. 604/368, 372
 See application file for complete search history.

(56) References Cited

U.S. PATENT DOCUMENTS

| | | | |
|---|---|---|---|
| 3,661,875 A | 5/1972 | Sieja |
| 3,699,103 A | 10/1972 | Kiss |
| 3,770,731 A | 11/1973 | Jaeger |
| 4,062,817 A | 12/1977 | Westerman |
| 4,076,663 A | 2/1978 | Masuda et al. |
| 4,093,776 A | 6/1978 | Aoki et al. |
| 4,454,055 A | 6/1984 | Richman et al. |
| 4,541,871 A | 9/1985 | Obayashi et al. |
| 4,587,308 A | 5/1986 | Makita et al. |
| 4,625,001 A | 11/1986 | Tsubakimoto et al. |
| 4,654,039 A | 3/1987 | Brandt et al. |

(Continued)

FOREIGN PATENT DOCUMENTS

| | | |
|---|---|---|
| EP | 47549 A1 | 10/1999 |
| JP | 11290682 A | 10/1999 |
| WO | WO-93 05080 A1 | 3/1993 |

*Primary Examiner* — Lynn Anderson
(74) *Attorney, Agent, or Firm* — Laura L. Whitmer; Amy M. Foust; Richard L. Alexander

(57) ABSTRACT

This invention is directed to super-absorbent material, which comprises a super absorbent polymer core that is coated with an organic, polar coating agent, and whereby the particulate super-absorbent material has a contact angle and a corresponding cos $CA_m$ (as defined herein), whereby the cos $CA_m$ is more than 0.3, and whereby, when said coating agent is in the form of particles, said coating agent particles have a (weight) mean particle size of from 0.001 to 1 micron. The material is useful for absorbent structures and absorbent articles (comprising such structures). The coated super-absorbent material is typically present in said absorbent structure at least at a concentration of 50% by weight of the structure, preferably even 80% or even 90%. The invention also provides a process for making the absorbent material.

6 Claims, 1 Drawing Sheet

(56) References Cited

U.S. PATENT DOCUMENTS

| | | | |
|---|---|---|---|
| 4,666,983 A | 5/1987 | Tsubakimoto et al. | |
| 4,673,402 A | 6/1987 | Weisman et al. | |
| 4,699,823 A * | 10/1987 | Kellenberger et al. | 428/219 |
| 4,734,478 A | 3/1988 | Tsubakimoto et al. | |
| RE32,649 E | 4/1988 | Brandt et al. | |
| 4,789,861 A | 12/1988 | Baggett et al. | |
| 4,824,901 A | 4/1989 | Alexander et al. | |
| 4,834,735 A | 5/1989 | Alemany et al. | |
| 4,935,022 A | 6/1990 | Lash et al. | |
| 5,164,459 A | 11/1992 | Kimura et al. | |
| 5,247,068 A | 9/1993 | Donachy et al. | |
| 5,374,684 A | 12/1994 | Tai | |
| 5,409,771 A | 4/1995 | Dahmen et al. | |
| 5,419,956 A | 5/1995 | Roe | |
| 5,562,646 A | 10/1996 | Goldman et al. | |
| 5,599,335 A | 2/1997 | Goldman et al. | |
| 5,611,885 A * | 3/1997 | Hansen et al. | 156/326 |
| 5,633,316 A | 5/1997 | Gartner et al. | |
| 5,728,742 A | 3/1998 | Staples et al. | |
| 5,744,564 A | 4/1998 | Stanley, Jr. et al. | |
| 6,107,358 A * | 8/2000 | Harada et al. | 521/133 |
| 6,124,391 A | 9/2000 | Sun et al. | |
| 7,745,685 B2 * | 6/2010 | Fell et al. | 604/359 |
| 2002/0040210 A1 * | 4/2002 | Luccio et al. | 604/367 |
| 2004/0106745 A1 * | 6/2004 | Nakashima et al. | 525/418 |
| 2004/0236016 A1 * | 11/2004 | Thornton et al. | 525/54.3 |
| 2005/0101927 A1 * | 5/2005 | Joseph et al. | 604/367 |

\* cited by examiner

ABSORBENT STRUCTURES COMPRISING COATED SUPER-ABSORBENT POLYMER PARTICLES

CROSS REFERENCE TO RELATED APPLICATIONS

This application is a Continuation of U.S. application Ser. No. 11/474,857, filed Jun. 26, 2006 now U.S. Pat. No. 7,311,968, which is a Divisional of U.S. application Ser. No. 10/881,090, filed Jun. 30, 2004 now U.S. Pat. No. 7,108,916, the substances of which are incorporated herein by reference.

FIELD OF THE INVENTION

This invention is directed to absorbent structures and disposable absorbent articles comprising particles of super-absorbent material, e.g. super-absorbent gelling material of a specific particle size, which is coated with an organic, polar coating agent. The super-absorbent (gelling) material is typically present in said absorbent structure at least at a concentration of 50% by weight of the structure, preferably even 80% or even 90%.

BACKGROUND OF THE INVENTION

An important component of disposable absorbent articles such as diapers is an absorbent core structure comprising super-absorbent polymers, or SAP's, which ensure that large amounts of bodily fluids, e.g. urine, can be absorbed by the article during its use. When the SAP's were first introduced in absorbent articles, a significant decrease in the article's thickness was achieved, because a much smaller volume of super-absorbent polymer was needed, compared to the large volumes of absorbent pulp, traditionally used in absorbent articles. See for example, U.S. Pat. No. 3,699,103 (Harper et al.), issued Jun. 13, 1972, and U.S. Pat. No. 3,770,731 (Harmon), issued Jun. 20, 1972, that disclose the use of such absorbent polymers in absorbent articles and see for example, U.S. Pat. No. 4,673,402 (Weisman et al.), issued Jun. 16, 1987 and U.S. Pat. No. 4,935,022 (Lash et al.), issued Jun. 19, 1990, that disclose dual-layer core structures comprising a fibrous matrix and absorbent polymers useful in fashioning thin, compact, non-bulky diapers.

These absorbent polymers are often made by initially polymerizing unsaturated carboxylic acids or derivatives thereof, such as acrylic acid, alkali metal (e.g., sodium and/or potassium) or ammonium salts of acrylic acid, alkyl acrylates, and the like in the presence of relatively small amounts of di- or poly-functional monomers such as N,N'-methylenebisacrylamide, trimethylolpropane triacrylate, ethylene glycol di(meth)acrylate, or trialkylamine. The di- or poly-functional monomer materials serve to lightly cross-link the polymer chains thereby rendering them water-insoluble, yet water-swell able. These lightly cross-linked absorbent polymers contain a multiplicity of carboxyl groups attached to the polymer backbone. These carboxyl groups generate an osmotic driving force for the absorption of body fluids by the cross linked polymer network.

Absorbent polymers useful as absorbents in absorbent members and articles such as disposable diapers need to have adequately high sorption capacity, as well as adequately high gel strength. Sorption capacity needs to be sufficiently high to enable the absorbent polymer to absorb significant amounts of the aqueous body fluids encountered during use of the absorbent article. Gel strength relates to the tendency of the swollen polymer particles to deform under an applied stress, and needs to be such that the particles do not deform and fill the capillary void spaces in the absorbent member or article to an unacceptable degree, so-called gel blocking, thereby inhibiting the rate of fluid uptake or the fluid distribution by the member or article. (Once gel-blocking occurs, it can substantially impede the distribution of fluids to relatively dry zones or regions in the absorbent member or article and leakage from the absorbent article can take place well before the particles of absorbent polymer in the absorbent article are fully saturated or before the fluid can diffuse or wick past the "blocking" particles into the rest of the absorbent article.)

In general, the permeability of a zone or layer comprising swollen absorbent polymer can be increased by increasing the cross link density of the polymer gel, thereby increasing the gel strength. However, this typically also reduces the absorbent capacity of the gel undesirably. See, for example, U.S. Pat. No. 4,654,039 (Brandt et al.), issued Mar. 31, 1987 (reissued Apr. 19, 1988 as U.S. Reissue Pat. 32,649) and U.S. Pat. No. 4,834,735 (Alemany et al.), issued May 30, 1989.

In the past decade, significant investments have been made to improve the performance of such SAP's, e.g. to provide a higher absorbent capacity per volume, to improve fluid distribution throughout the SAP's, to reduce so-called gel blocking of the SAP's.

At relatively high concentrations, an important property of these absorbent polymers is their permeability/flow conductivity. The permeability/flow conductivity of a material can be defined in terms of its Saline Flow Conductivity (SFC). SFC is a measure of the ability of a material to transport saline fluids, such as the ability of a layer comprising swollen absorbent polymer to transport body fluids. Typically, an air-laid web of pulp fibers (e.g., having a density of 0.15 g/cc) will exhibit an SFC value of about $200 \times 10^{-7}$ $cm^3 \cdot sec/g$.

Absorbent polymers with relatively high permeability (SFC values) can be made by increasing the level of cross linking, which increases the strength of the swollen gel, but this typically also reduces the absorbent capacity of the gel undesirably, as described above. The key focus has so far been to modify the surface cross-linking such that an optimum SFC value and absorbent capacity are achieved at the same time, e.g. such that one does not compromise the other too much.

In addition to surface cross linking, several other approaches have been utilized to improve the permeability, and/or the absorption rate of the absorbent. For example, U.S. Pat. No. 5,419,956 (Roe), issued on May 30, 1995, describes the addition of inorganic particles such as silica to super-absorbent polymers to improve fluid uptake rate and to increase fluid distribution. U.S. Pat. No. 4,454,055 (Richman) describes the addition (either under wet or dry conditions) of between 1 and 75% of an extender material such as cellulose derivatives, or inorganic materials like clay or minerals. The objective of this development is an increase of absorbent capacity. It should also be noted that silica and certain inorganic powders and also wax have been used as process aids when producing super absorbent polymer particles, namely as anti caking agents, see for example U.S. Pat. No. 6,124,391. The inorganic material or the wax is then typically not present in the form of a real coating, although the super absorbent polymers may be partially coated with this material.

However, there is still a need to improve the absorbent capacity and gel strength at the same time.

Also there is still a need to provide even thinner absorbent articles, e.g. sanitary napkins and diapers. One way of doing this is to reduce the amount of fibers used in the absorbent cores of the articles, or even not to incorporate any fibers at all in the absorbent cores, but only super absorbent polymers. As described above, reducing the fiber content between the super-absorbent polymers increases the risk of gel blocking. Thus, there is a need to provide thinner cores with out much or any fibers, which do not suffer from gel blocking.

The inventors have now found an improved super absorbent material that provides higher SFC values and higher gel strength and that does not suffer from gel blocking and that even can be used in fiber-free absorbent structures.

They found that it is important to ensure that the super absorbent material provides high capillary forces. The inventors found that it is thereto important that the super-absorbent material has a specific low contact angle, correlated with a specific surface energy and that the liquid to be absorbed has to remain a specific surface tension, e.g. should not reduce too much in surface tension. It is believed that this has so far not been recognized in the art. In fact, it has been found that the coating used in the prior art, such as hydrophilic silica, may negatively affects the contact angle and the related surface energy of the super absorbent material and therefore this type of coated super absorbent material does not provide the required capillary forces. Equally, surfactants, which are also used in super absorbent materials, can significantly reduce the capillary forces due to the effect they have on the surface tension of the liquid and the surface energy of the material.

The inventors found that certain specific coatings can provide the required surface energy of the super absorbent material, whilst not negatively affecting the surface tension of the liquid to be absorbed. They found that the coating has to comprise a specific organic coating material with one or more polar groups, which typically is relatively small as not to change the liquid's surface tension too much, even when the coating material is water-soluble.

They found that absorbent structures or articles comprising such coated super absorbent polymers not only provide excellent SFC and gel strength values at the same time, but that such absorbent structures can also be fiber-free, and hence thinner, without the risk of gel blocking.

In addition, the absorbent structures or articles have higher capillary forces leading to a better drainage of the layer(s) closest to the wearer's skin, and to a better liquid spreading or wicking over the length and width of the absorbent structure.

SUMMARY OF THE INVENTION

The present invention relates to a particulate super-absorbent material comprising a particulate core of super-absorbent polymers, coated with a coating agent, comprising or being an organic coating compound, which has one or more polar groups, and whereby the particulate super-absorbent material has a contact angle and a corresponding cos $CA_m$ (as defined herein), whereby the cos $CA_m$ is more than 0.3, and whereby, when said coating agent is in the form of particles, said coating agent particles have a (weight) mean particle size of from 0.001 to 1 micron and preferably no coating agent particles with a particle size of more than 50 microns are present.

The invention also provides a particulate super-absorbent material comprising a particulate core of super-absorbent polymers, coated with a coating agent, comprising or being an organic coating compound, which has one or more polar groups, said coating agent of said particulate super-absorbent material providing a surface tension reduction of less than 10%, or even less than 5% or even about 0%, and whereby, when said coating agent is in the form of particles, said coating agent particles have a (weight) mean particle size of from 0.001 to 1 micron and preferably no coating agent particles with a particle size of more than 50 microns are present.

The invention also provides specific absorbent structures and articles comprising the coated super absorbent material of the invention; it also provides specific articles whereby the coating agent is present in a gradient manner, i.e. whereby an area in an absorbent structure comprises more coating agent than another area.

The invention also provides processes for making the coated super absorbent material of the invention and preferred coating steps.

The invention also relates to the use of an organic coating agent on a core of super absorbent polymers to provide either: a $FHA_{coated}$ (20 cm) value of the coated super absorbent material which is higher than $FHA_{uncoated}$ (20 cm) value of the uncoated core; or a positive Δ D (delta diffusion constant), which is $(D_{coated\ super\ absorbent\ material}) - (D_{uncoated\ super\ absorbent\ polymers})$, whereby each respective D=(FHA(20 cm))×(SFC).

DETAILED DESCRIPTION OF THE INVENTION

Super Absorbent Polymers

Figure 1:
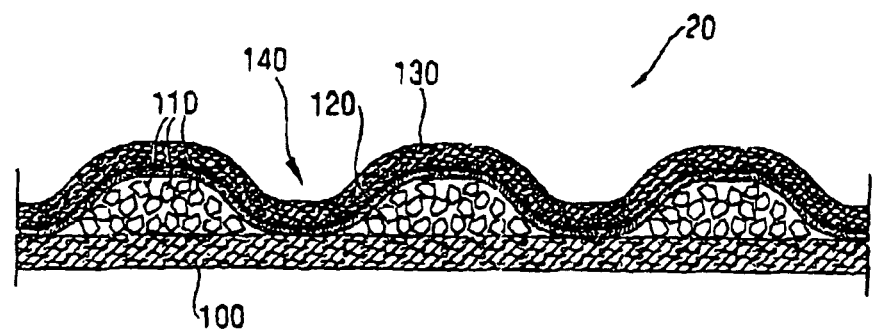
FIG. 1 shows a cross-sectional view of a preferred absorbent structure of the invention.

As used herein, the term "super absorbent polymer" refers to a polymer, which is water-insoluble, water-swell able or gelling, and which has a Gel Volume (GV) of at least 10 g/g. These polymers are typically lightly cross-linked polymers, which contain a multiplicity of acid functional groups such as carboxylic acid groups. Examples of acid polymers suitable for use herein include those which are prepared from polymerizable, acid-containing monomers, or monomers containing functional groups which can be converted to acid groups after polymerization. Thus, such monomers include olefinically unsaturated carboxylic acids and anhydrides, and mixtures thereof. The acid polymers can also comprise polymers that are not prepared from olefinically unsaturated monomers.

Examples of such polymers include polysaccharide-based polymers such as carboxymethyl starch and carboxymethyl cellulose, and poly(amino acid) based polymers such as poly (aspartic acid). For a description of poly(amino acid) absorbent polymers, see, for example, U.S. Pat. No. 5,247,068, issued Sep. 21, 1993 to Donachy et al., which is incorporated herein by reference.

Some non-acid monomers can also be included, usually in minor amounts, in preparing the absorbent polymers herein. Such non-acid monomers can include, for example, monomers containing the following types of functional groups: carboxylate or sulfonate esters, hydroxyl groups, amide-groups, amino groups, nitrile groups, quaternary ammonium salt groups, and aryl groups (e.g., phenyl groups, such as those derived from styrene monomer). Other optional non-acid monomers include unsaturated hydrocarbons such as ethylene, propylene, 1-butene, butadiene, and isoprene. These non-acid monomers are well-known materials and are described in greater detail, for example, in U.S. Pat. No. 4,076,663 (Masuda et al.), issued Feb. 28, 1978, and in U.S. Pat. No. 4,062,817 (Westerman), issued Dec. 13, 1977.

Olefinically unsaturated carboxylic acid and anhydride monomers useful herein include the acrylic acids typified by acrylic acid itself, methacrylic acid, α-chloroacrylic acid, a-cyanoacrylic acid, β-methylacrylic acid (crotonic acid), α-phenylacrylic acid, β-acryloxypropionic acid, sorbic acid, α-chlorosorbic acid, angelic acid, cinnamic acid, p-chlorocinnamic acid, β-stearylacrylic acid, itaconic acid, citroconic acid, mesaconic acid, glutaconic acid, aconitic acid, maleic acid, fumaric acid, tricarboxyethylene, and maleic anhydride.

Preferred super-absorbent polymers contain carboxyl groups. These polymers include hydrolyzed starch-acrylonitrile graft copolymers, partially neutralized hydrolyzed starch-acrylonitrile graft copolymers, starch-acrylic acid graft copolymers, partially neutralized starch-acrylic acid graft copolymers, hydrolyzed vinyl acetate-acrylic ester copolymers, hydrolyzed acrylonitrile or acrylamide copolymers, slightly network cross linked polymers of any of the foregoing copolymers, polyacrylic acid, and slightly network cross linked polymers of polyacrylic acid. These polymers can be used either solely or in the form of a mixture of two or more different polymers. Examples of these polymer materials are disclosed in U.S. Pat. No. 3,661,875, U.S. Pat. No. 4,076,663, U.S. Pat. No. 4,093,776, U.S. Pat. No. 4,666,983, and U.S. Pat. No. 4,734,478.

Most preferred polymer materials used for making the super-absorbent polymers herein are polyacrylates/acrylic acids and derivatives thereof, preferably (slightly) network cross linked polymers partially neutralized polyacrylic acids and/or -starch derivatives thereof.

Most preferably, the absorbent polymers comprise from about 50-95, preferably about 75% neutralized, (slightly) network cross-linked, polyacrylic acid (i.e., poly (sodium acrylate/acrylic acid)). Network cross-linking renders the polymer substantially water-insoluble and, in part, determines the absorptive capacity and extractable polymer content characteristics of the absorbent polymers. Processes for network cross linking these polymers and typical network cross linking agents are described in greater detail in U.S. Pat. No. 4,076,663.

While the absorbent polymer is preferably of one type (i.e., homogeneous), mixtures of absorbent polymers can also be used in the present invention. For example, mixtures of starch-acrylic acid graft copolymers and slightly network crosslinked polymers of polyacrylic acid can be used in the present invention. Mixtures of (coated) polymers with different physical properties, and optionally also different chemical properties, could also be used, e.g. different mean particle size, absorbent capacity, absorbent speed, SFC value).

In absorbent structures or articles according to the present invention, there can be used one and the same super-absorbent polymer type or material throughout the total structure, or there can be different types or materials in different parts of the structure. A super-absorbent material or composition can have the same concentration throughout the structure, or can be at varying concentrations distributed there through.

Specifically, said coated super-absorbent particles can be uniformly distributed throughout the total structure of an absorbent article or structure, or there can be a gradient in the amount of super absorbent per volume unit, type, or property within the structure. This gradient can e.g. be achieved when said coating of the super absorbent is selectively applied to only a part of the super absorbent of said absorbent article or structure.

For the uncoated super absorbent polymer particles of the structures of the present invention, the particle size is preferably such that at least 90% or even at least 99% of the particles is between 45 and 850 microns, or even between 100 and 800 microns, or even between 150 and 710 microns; the mean particle size of the uncoated super absorbent polymer particles is preferably from 150 to 600, or even from 200 to 500 or even 250 to 450 microns.

The particle sizes and mean particle sizes above equally apply to the coated super absorbent polymers, as comprised by the super absorbent material herein, since the coating typically does not change the particle size much.

It is also preferred herein that the coated an uncoated super absorbent polymer particles have a specific surface area of at least 0.01 m$^2$ per gram, preferably at least 0.1 m$^2$ per gram, and more preferable at least 0.25 m$^2$ per gram in accordance with the specific surface evaluation method as defined e.g. in "Modern Super Absorbent Technology" by F. L. Buchholz and A. T. Graham, published by Wiley VCH, New York, 1998.

For the purposes of this invention, particle size distributions are determined according to the method described in the Test Methods section of U.S. Pat. No. 5,419,956 (Roe et al).

The absorbent polymers useful in the present invention can be formed by any polymerization and/or cross-linking techniques. Typical processes for producing these polymers are described in U.S. Reissue Pat. 32,649 (Brandt et al.), issued Apr. 19, 1988, U.S. Pat. No. 4,666,983 (Tsubakimoto et al.), issued May 19, 1987, and U.S. Pat. No. 4,625,001 (Tsubakimoto et al.), issued Nov. 25, 1986. Cross-linking can be affected during polymerization by incorporation of suitable cross-linking monomers. Alternatively, the polymers can be cross-linked after polymerization by reaction with a suitable reactive cross-linking agent. Surface cross-linking of the initially formed polymers is a preferred way to control to some extends the absorbent capacity, porosity and permeability.

Suitable general methods for carrying out surface cross linking of absorbent polymers according to the present invention are disclosed in U.S. Pat. No. 4,541,871 (Obayashi), issued Sep. 17, 1985; published PCT application WO92/16565 (Stanley), published Oct. 1, 1992, published PCT application WO90/08789 (Tai), published Aug. 9, 1990; published PCT application WO93/05080 (Stanley), published Mar. 18, 1993; U.S. Pat. No. 4,824,901 (Alexander), issued Apr. 25, 1989; U.S. Pat. No. 4,789,861 (Johnson), issued Jan. 17, 1989; U.S. Pat. No. 4,587,308 (Makita), issued May 6, 1986; U.S. Pat. No. 4,734,478 (Tsubakimoto), issued Mar. 29, 1988; U.S. Pat. No. 5,164,459 (Kimura et al.), issued Nov. 17, 1992; published German patent application 4,020,780 (Dahmen), published Aug. 29, 1991; and published European patent application 509,708 (Gartner), published Oct. 21, 1992.

Coating Agents

The coating agent herein comprises or consists of one or more organic compound(s) as defined herein. Preferably, when the coating agent comprises the organic compound(s) as defined herein and also other (minor) ingredients, the organic compound(s) represent(s) at least 60% by weight of the coating agent, or even at least 75% or even at least 85% or even at least 95% by weight of the coating agent.

The organic compound of the coating agent has at least one polar group. The coating agent is such that the resulting coated particulate super absorbent material has a contact angle and a corresponding cos $CA_m$ (as defined herein), whereby the cos $CA_m$ is more than 0.3.

Furthermore, the coating agent is typically such that it does not reduce the surface tension much, when it, or the super absorbent material of the invention, is present in (saline) water, as defined by the test hereinafter, e.g. the coating agent provides only a surface tension reduction of less than 10%, or even less than 5% or even about 0%.

Preferably, the coating agent is permanent, i.e. it does not migrate or dissolve when the coated super absorbent material is brought in contact with urine or (saline) water, and/or if any coating agent does migrate or dissolve in the urine or (saline) water, it does not reduce the surface tension much, as described above.

The coating agent is typically such that the contact angle of the coated super-absorbent material is changed versus the contact angle of the uncoated super absorbent polymer core, i.e. such that the uncoated super absorbent polymer core before being coated with said coating agent, has a certain contact angle $CA_p$ and a cos $CA_p$ (as defined herein) and the particulate super absorbent material has a certain contact angle $CA_m$ and a cos $CA_m$ (as defined herein), and the ratio cos $CA_m$/cos $CA_p$ is at least 1.5.

The coating agent can be applied by the methods described below, including by dry mixing of the super absorbent polymer material with particles of the coating agent. If the coating agent is in the form of particles, said coating agent particles have a mean particle size of from 0.001 to 1 micron and preferably no particles with a particle size of more than 50 microns are present.

Preferred organic coating agents herein have one or more polar groups and a low molecular weight, preferably a molecular weight of less than 1000 mol, or even less than 750 mol or even less than 500 mol.

Preferred organic coating agents herein are water miscible organic compound that provide a surface tension reduction of 15% or less, or even preferable 10% or less, or even less than 5% or even about 0%, as can be determined with the test set out herein.

Preferred as coating agent, or component thereof, are water miscible organic compounds having 2 to 9 carbon atoms, preferably in single linear or branched chain, and in addition at least one polar group comprising at least one oxygen atom bound to a hydrogen atom. (If the polar group contains one or more carbon atom, then this is not included in the 2-9 carbon atoms in the compound.).

Preferred are polar groups having an O—H group. Preferred is also that the organic compound or component of the coating agent is an organic derivates of an oxo acid, or salt or ester thereof. Typical are derivatives of oxo acids of carbon, sulfur, phosphor; thus, the organic compounds or components of the coating agent herein are for example derivatives of a carboxylic acid, phosphoric acid and/or sulphoric acid.

Preferably, the coating agent comprises a compound that has at least two polar groups, preferably at least one cationic group (preferably an amine group, guanidine group), most preferably at least one cationic and at least one anionic polar group.

Namely, it has been found that especially organic compounds that have a cationic group may be or provide permanent coating agent, as described above, resulting in a low or no surface tension reduction, as can be determined by the test defined herein.

Preferred coating agents comprise one or more of the following group: N-(2-Acetamido)-2-aminoethansulfonic-acid, N-(2-Acetamido)-imino-di-acetic-acid, N-acetyl-glycin, β-Alanine, Aluminum-hydroxy-acetate, N-Amidino-glycine, 2-Amino-ethyl-hydrogenphosphate, 2-Amino-ethyl-hydrogensulfate, Amino-methan-sulfonic-acid, Maleinic-acid, Arginine, Asparaginic-acid, Butane-di-acid, Bis(1-aminoguanidinium)-sulfate, 2-Oxo-propionic-acid, Tri-Calcium-di-citrate, Calciumgluconate, Calcium-saccharate, Calcium-Titriplex®, Carnitine, Cellobiose, Citrulline, Creatine, Dimethylaminoacetic acid, Than-1,2-disulfonic-acid, Ethylendiammoniumsulfate, Fructose, Fumaric-acid, Galactose, Glucosamine, Gluconic-acid, Glutamine, 2-Amino-glutaric-acid, Glutaric-acid, Glycine, Glycylglycine, Imino-di-acetic-acid, Magnesium-glycerophosphate, Oxalicacid, Tetrahydroxy-adipinic-acid, Taurine, N-Methyl-taurin, Tris-(hydroxymethyl)-aminomethane, N-(Tris-(hydroxymethyl)-methyl)-2-aminoethansulfonicacid.

Coating Process

Any known process for coating particles can be used to make the coated super-absorbent material herein. A process and the process conditions are preferably selected such that the resulting coating is applied over about the whole surface of the polymer core.

Preferred maybe that the prior to coating with the coating agent, a coating aid is applied (e.g. to the polymer cores or to a structure comprising the polymer cores), which subsequently helps to hold the coating agent in place, e.g. a viscous or sticky material may serve as coating aid.

It may be more preferred even, in order to get a good coating, to apply the coating agent in the form of a solution, slurry or suspension, and/or by known spray-drying processes, fluid bed processes, or by dip coating.

In another preferred execution, the coating agent may be blended or mixed in the dry state with the super-absorbent polymer cores, or with a structure comprising the polymer cores.

An exemplary process for the present invention involves dry mixing the particulate coating agent and the super-absorbent polymers, forming the core, in a tumble mixer for 30 minutes. The resulting material can then be sieved, to obtain a coated super-absorbent material of the invention with the required coating level and of the required particle size.

The mixing or blending process should further be as gentle as possible so as to minimize the extent of abrasion and/or breakage of the absorbent polymer particles. The mixing process (and also the other processes described herein) may be done in a continuous process, or in a batch wise fashion.

Preferred suitable equipment for such a gentle process is generally known to one skilled in the art, such as ploughshare mixer as available from Gebr. Lödge Maschinenbau GmbH, Germany, under the designation KM as continuous mixer, or FM as batch mixer, or as continuous mixer from Schugi B V, Netherlands, or as batch mixer from H. Forberg, Norway.

Absorbent Structures and Articles

The absorbent structure of one embodiment of the invention is typically for use in disposable absorbent articles, such as preferably interlabial products, sanitary napkins, panty liners, and preferably adult incontinent products, diapers and training pants.

These preferred absorbent articles typically comprise a liquid impervious (but preferably gas pervious) backsheet, a fluid pervious topsheet joined to, or otherwise associated with the backsheet, and the absorbent structure according to the present invention positioned between the backsheet and the topsheet. Such articles are well known in the art and fully disclosed in various documents mentioned throughout the description such as U.S. Pat. No. 5,599,335 (Goldman et al.).

Typically, the absorbent structure of the invention is that part of an absorbent article which serves to store the bodily fluid, e.g. the storage layer of an absorbent article. As known in the art, this may be in direct contact with an acquisition layer, or in one embodiment of the invention, it may form a unitary structure with an acquisition layer. In yet another embodiment of the invention the absorbent structure is an acquisition layer for use in an absorbent article.

The absorbent structure may comprise the super-absorbent material at any weight level or concentration, but preferably, in particular when the absorbent structure serves as a storage layer, or when the absorbent structure comprises a layer that serves as storage layer, the structure or layer comprises large amounts of the super absorbent material herein, compared to possible other components of the structure, i.e. preferably more than 50% or even more than 70% or even more than 80% or even more than 90% of the super absorbent material herein, by weight of the structure or (storage) layer thereof.

For example, the super absorbent material may be mixed with absorbent fibrous material, such as airfelt material, which can provide a matrix for immobilization of the superabsorbent polymer material. However, preferably a relatively low amount of absorbent fibrous (cellulose) material is used in the absorbent structure. Thus, if the absorbent structure is a liquid storage layer or when the absorbent structure comprises one or more liquid storage layers, it may be preferred that said liquid structure or said liquid storage layer comprises large amounts of the super absorbent material herein and only very little or no absorbent (cellulose) fibers, e.g. preferably less than 40% weight of that layer, or even less than 20% by weight or even less than 10 weight % or even less than 5% by weight of absorbent fibrous (cellulose) material, and preferably more than 50% or even more than 70% or even more than 80% or even more than 90% of the super absorbent material herein.

The absorbent structure may comprise a wrapping material, which wraps the portion comprising the super absorbent material, a so-called core wrap material. In one preferred embodiment the core wrap material comprises a top layer and a bottom layer, being furthest away from the skin of the user. The core wrap material, the top layer or the bottom layer can be provided from a non-woven material. One preferred material is a so-called SMS material, comprising a spunbonded, a melt-blown and a further spunbonded layer. Highly preferred are permanently hydrophilic non-wovens, and in particular non-wovens with durably hydrophilic coatings. An alternative preferred material comprises a SMMS-structure. The top layer and the bottom layer may be provided from two or more separate sheets of materials or they may be alternatively provided from a unitary sheet of material Preferred non-woven materials are provided from synthetic fibers, such as PE, PET and most preferably PP. As the polymers used for nonwoven production are inherently hydrophobic, they are preferably coated with hydrophilic coatings, e.g. coated with nanoparticles, as known in the art.

Notably, permanently hydrophilic non-wovens are also useful in other parts of an absorbent article, for example as or in the topsheet.

In a preferred embodiment of the present invention the absorbent structure comprises a wrapping material, the super absorbent material, described herein, and a thermoplastic material and/or a layer of adhesive, which may be a (non-absorbing) fibrous layer of adhesive.

A preferred absorbent structure (20) of the invention is shown in FIG. 1. The layer of super absorbent material (110) as described herein, is preferably a layer comprising openings (140). Typically these openings have a diameter or largest span of less than 10 mm, preferably less than 5 mm, 3 mm, or even less than 2 mm and preferably of more than 0.5 mm, 1 mm or 1.5 mm. The absorbent structure (20) may also comprise a thermoplastic composition that serves to at least partially immobilize the absorbent material.

In a preferred embodiment of the present invention the thermoplastic material is provided as a non-absorbing, fibrous adhesive layer (120), which is partially in contact with the super absorbent material layer (110) and partially in contact with the wrapping material (130). The overlaying wrapping material (130) may be a unitary material together with the underlying wrapping material (100), or the underlying wrapping material (100) and the overlaying wrapping material (130) could be separate materials.

The adhesive layer (120) fills the openings (140) between the super absorbent material (110). This imparts an essentially three-dimensional structure to the fibrous layer of thermoplastic material (120).

Figure 2:
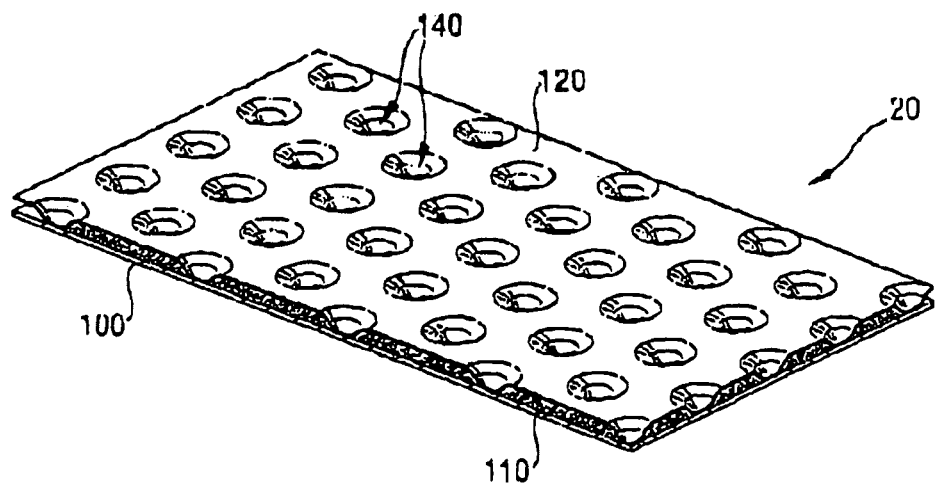
FIG. 2 shows a perspective view of the absorbent structure of FIG. 1.

The preferred absorbent structure (20) of FIG. 1 is also shown in FIG. 2 as a perspective view.

The absorbent structure (20) of FIG. 2 can be placed between a topsheet and a backsheet of a disposable absorbent article, such as a diaper, in accord with the present invention.

Such preferred absorbent structures can for example be made as follows:
a) providing a substrate material that can serve as a wrapping material;
b) depositing super absorbent material onto a first surface of the substrate material, preferably in a pattern comprising at least one zone which is substantially free of absorbent material, and the pattern comprising at least one zone comprising absorbent material, preferably such that opening are formed between the super-absorbent material;
c) depositing a thermoplastic material onto the first surface of the substrate material and the super absorbent material, such that portions of the thermoplastic material are in direct contact with the first surface of the substrate and portions of the thermoplastic material are in direct contact with the absorbent material;
d) and then typically closing the above by folding the substrate material over, or by placing another substrate matter over the above.

The thermoplastic material or layer can comprise any thermoplastic composition, preferred are adhesive thermoplastic compositions, also referred to as hot melt adhesives.

The thermoplastic or adhesive material is subject to external forces when the super absorbent material has acquired liquid and swells. Thus, a preferred thermoplastic or adhesive will allow for such swelling, without breaking and without imparting too many compressive forces, which would restrain the super absorbent material from swelling.

The thermoplastic material has typically a glass transition temperature (Tg) below room temperature (20° C.). Exemplary polymers useful in the thermoplastic material are (styrenic) block copolymers including A-B-A triblock structures, A-B diblock structures and (A-B)n radial block copolymer structures wherein the A blocks are non-elastomeric polymer blocks, typically comprising polystyrene, and the B blocks are unsaturated conjugated diene or (partly) hydrogenated versions of such. The B block is typically isoprene, butadiene, ethylene/butylene (hydrogenated butadiene), ethylene/propylene (hydrogenated isoprene), and mixtures thereof.

Other suitable thermoplastic polymers that may be employed are metallocene polyolefins, which are ethylene polymers prepared using single-site or metallocene catalysts. Therein, at least one comonomer can be polymerized with ethylene to make a copolymer, terpolymer or higher order polymer. Also applicable are amorphous polyolefins or amorphous polyalphaolefins (APAO) which are homopolymers, copolymers or terpolymers of C2 to C8 alphaolefins.

The thermoplastic material preferably also comprises a resin and a plasticizer. The resin has typically a Mw below 5,000 and a Tg usually above room temperature, typical concentrations of the resin in a hot melt are in the range of 30-60%. The plasticizer has a low Mw of typically less than 1,000 and a Tg below room temperature, a typical concentration is 0-15%.

Preferably the thermoplastic material or adhesive is present in the forms of non-absorbing fibres throughout, i.e. the thermoplastic material or adhesive is fiberized. Preferably, the fibres will have an average thickness of 1-50 micrometer and an average length of 5 mm to 50 cm.

Preferred disposable absorbent article herein are sanitary napkins, panty liners, adult incontinence products and infant diapers or training or pull-on pants, whereby articles which serve to absorb urine, e.g. adult incontinence products, diapers and training or pull-on pants are most preferred articles herein, since they most benefit from the absorbent structure of the present invention.

Preferred articles herein have a topsheet and a backsheet, which each have a front region, back region and crotch region, positioned therein between. The absorbent structure of the invention is typically positioned in between the topsheet and backsheet. Preferred backsheets are vapour pervious but liquid impervious. Preferred topsheet materials are at least partially hydrophilic; preferred are also so-called apertured topsheets. Preferred maybe that the topsheet comprises a skin care composition, e.g. a lotion.

A preferred diaper or training pants herein has a front waist band and a back waist band, whereby the front waist band and back waist band each have a first end portion and a second end portions and a middle portion located between the end portions, and whereby preferably the end portions comprise each a fastening system, to fasten the front waist band to the rear waist band or whereby preferably the end portions are connected to one another, and whereby the middle portion of the back waist band and/or the back region of the backsheet and/or the crotch region of the backsheet comprises a landing member, preferably the landing member comprising second engaging elements selected from loops, hooks, slots, slits, buttons, magnets. Most preferred are hooks, adhesive or cohesive second engaging elements. Preferred may be that the engaging elements on the article, or preferably diaper are provided with a means to ensure they are only engage able at certain moments, for example, they may be covered by a removable tab, which is removed when the engaging elements are to be engaged and may be re-closed when engagement is no longer needed, as described above.

Preferred diapers and training pants herein have one or more sets of leg elastics and/or barrier leg cuffs, as known in the art.

Preferred may also be that the topsheet has a large opening, preferably with elastication means along the length thereof, where through waist material can pass into a void space above the absorbent structure, and which ensures it is isolated in this void space, away from the wearer's skin.

Test Methods Used Herein:
Saline Flow Conductivity (SFC)

A measure of permeability and an indication of porosity is provided by the saline flow conductivity of the gel bed as described in U.S. Pat. No. 5,562,646, (Goldman et al.) issued Oct. 8, 1996.

Gel Volume Determination (GV)

This test is described in U.S. Pat. No. 4,654,039 (Brandt et al.) issued Mar. 31, 1987. The test determines the amount of synthetic urine solution imbibed by absorbent polymers that are in contact with the solution Extractables or Extractable Polymers Value Another important characteristic of particularly preferred super absorbent material and super absorbent polymers useful in the present invention is the level of extractable polymer material or extractables present therein. Evaluation and explanation of which levels of extractable polymer is still acceptable is disclosed and explained in detail in U.S. Pat. No. 5,599,335. As a general rule the extractable amount should be as low as possible and the lower it is the less undesired reaction the extractable material can cause. Preferred are levels of extractables of less than 10% by weight.

FHA (Fixed Height Absorption) Value

FHA measurements are essentially the same as PUP measurements, as defined in U.S. Pat. No. 5,599,335 (PUP=performance under pressure capacity), but instead made against a gravimetric height, i.e. the liquid is absorbed by pulling it against gravity. As PUP, FHA values are given in units of g/g (gram absorbed/gram material). FHA values need to be identified by reference to the respective hydrostatic pressure, which has been overcome, e.g. at a pressure of two, three, and fife kilopascal, which correspondents to the FHA at 20 cm, 30 cm or 50 cm, as used herein.

The fixed height absorption method evaluates the capillary pressure of a test fluid loaded SAP sample, i.e. the ability of a sample (bed) of (coated) SAP particles to draw test fluid in against a hydrostatic pressure.

(Coated) SAP absorb fluid in two ways, first in incorporating the fluid in its structure (swelling) driven by osmotic forces, second the SAP form a gel bed with interstitial capillaries, which are also filled and which achieve the transport of fluid to (coated) SAP particles not in direct contact to the fluid interface. If a loaded (coated) SAP sample (bed), loaded near to its theoretical capacity, can still exert high capillary pressure, then the SAP is used to its optimum extend, i.e. no SAP is wasted. The measurement essentially measures the amount of fluid absorbed by a sample which liquid is pulled against gravity over a fixed height.

The equipment used in the FHA method consist of the following:

a fluid reservoir with a "Mariotte-Tube" to define the 0 height fluid level Ho independent of fluid consumption during measurement a valve in a connecting tube between fluid reservoir and bottom of a funnel with glass-frit, a glass frit having a pore size 4 (i.e. 4-5.5 microns), where the glass frit is positioned so that the upper frit surface defines the measurement height Hm, a sample holder assembly comprising a cylinder made of Plexiglas with an inner diameter of 6 cm.

A disc of 5.9 cm diameter for placement onto the SAP sample, which disc fits without friction into the cylinder and a weight, which has a slightly smaller diameter than the disc and provides together with the disc a pressure of 2068 Pa (0.3 psi) onto the sample.

When combined the (coated) SAP is capable to acquire liquid from the frit and swell in height against a confining pressure of 2068 Pa (0.3 psi). The glass materials can be obtained in any usual chemical supply store, e.g. from VWR International GmbH, Vertriebszentrum Frankfurt, Insterburgerstrasse 9, D-60487 Frankfurt/M., Germany. The Plexiglas equipment and weight can be made by any skilled model work shop, e.g. Acryl & Modellbau, Peter Lorenz, Ruppertshainer Str. 14, D-65779 Kelkheim/Fischbach, Germany. In case Plexiglas is available or no model workshop can be found similar equipment can also be made from glass or stainless steel. All fittings, seals, and auxiliary laboratory equipment necessary need to be selected from equipment useful under good laboratory practices and the accuracy necessary for chemical laboratory evaluations.

It is further necessary to have a scale capable to measure up to 1/100 g for measuring the coated super absorbent material and uncoated SAP and the amount of fluid acquired by each material. Also for conducting the test it is necessary to put a layer of tissue between the glass frit surface and the actual sample to prevent (coated) super-absorbent polymer particles from entering the glass frit void spaces. The tissue is preferably a high wet strength tissue, cut to squares of 65 mm. The tissue needs to be thin and a 22.5 g/m² is useful. Such tissues are available from Frippa, Germany, as HWS 22.5 g/m² (gram per square meter) tissue or can be obtained from P&G, c/o R&D-STC, attention Mr. Bruno Ehrnsperger.

For the test standard laboratory conditions (21-23° C., 50% relative humidity) are used. For each test measurements 0.9 g coated super absorbent material or uncoated super absorbent polymers is weighted to the nearest 1/100 g; per height (e.g. 20 cm, as used herein) and per material, at least 3 samples need to be measured, to obtain an average of 3 measurements. The test liquid is 0.9% saline solution. The tissue is cut and attached to the sample holder without wrinkles. On the attached tissue the 0.9 g of AGM is evenly distributed. Then the sample holder is placed on the frit, which is already set to desired height (e.g.: 20 cm, which is 20 cm (or in other tests 30 cm or 50 cm) above the height of the meniscus at the bottom of the Mariotte tube. The valve is opened to allow liquid contact and the duration of the exposure to liquid is 60 minutes, to allow substantial saturation. At the end of this time the additional weight of the wet sample is measured as the amount of absorbed saline solution (this can be done by weighing the whole sample holder assembly initially and after the test, subtracting these numbers). The weight measurements are noted down to the nearest 1/100 g. The resulting FHA value as used herein in gram/gram is the average of at least 3 samples.

For the present invention, it is important that the $FHA_{coated}$ (20 cm) of the coated super absorbent material is higher than of the $FHA_{uncoated}$ (20 cm) of the uncoated super absorbent polymers, typically such that the ratio $FHA_{coated}$ (20 cm) to $FHA_{uncoated}$ (20 cm) is at least 1.05 or even at least 1.1 or even at least 1.2 or even at least 1.3.

This test can be equally conducted for the FHA (30 cm) and FHA (50 cm).

For the present invention, the $FHA_{coated}$ (30 cm) of the coated super absorbent material is higher than of the $FHA_{coated}$ (30 cm) of the uncoated super absorbent polymers, typically such that the ratio $FHA_{coated}$ (30 cm) to $FHA_{coated}$ (30 cm) is at least 1.1 or even at least 1.2 or even at least 1.3.

Typically, the ratio $FHA_{coated}$ (50 cm) to $FHA_{uncoated}$ (50 cm) is at least 1.2 or even at least 1.3 or even at least 1.4.

Contact Angle Measurement

This contact angle test as used herein is according to the Washbourn Sorption Method (see for example: "Contact Angles on Particles and Plates", Colloids and Surfaces, 27 (1987) 57-64; 2) or Krüss Technical Note TN302 & Application Note AN206.

The capillarity of absorbent structures comprising super-absorbent polymer particles or coated super absorbent polymer particles, i.e. super absorbent material of the invention depends, amongst others on the contact angle of the fluid that wets the particles or particulate material.

The contact angle of smooth surfaces can be easily determined via drop shape analysis. For a powder, two liquid wicking experiments are generally used to determine the contact angle, e.g. one experiment with heptane (as in the literature described, with an assumed contact angle of zero) and one with saline water.

The contact angle of the coated super-absorbent material and of the uncoated super-absorbent polymer particles, as used herein, is the contact angle with saline water, measured under the conditions below.

Thus, to obtain the experimental data, the constant 'c' (see below) has to be determined first, since this is needed in the equation to calculate the contact angle. The constant 'c' is obtained by measurement of the material with n-heptane.

The equipment used to do the measurements is preferably:
Krüss Processor Tensiometer K12 with Krüss software K121 or equivalent Data acquisition rate: 3 weight measurements per second
Sample holder, Krüss FL 12 Supplemented with a metal mesh (to keep the powder in the holder) Stainless steel 1.4401, ASTM Mesh 400, Pore width 38 μm Washburn Theory and Formulas used herein.

$$t = A\,m^2 \quad t = \text{Time after the solid touched the liquid surface} \tag{1}$$

$A$ = Constant, proportionality factor $m^2$ = Squared fluid mass drawn into pores of the solid $$A = \frac{\eta}{c\rho^2 \sigma \cos\Theta} \quad \eta = \text{Viscosity of liquid} \tag{2}$$

$\rho^2$ = Squared density of liquid $\sigma$ = Surface tension of liquid $c$ = Geometric constant of porous solid (powder)

$$\cos\Theta = \frac{m^2}{t}\,\frac{\eta}{c\rho^2 \sigma} \quad \text{In the experiment the fluid} \tag{3}$$
$$(1+2)$$

uptake squared vs. time is measured.

The initial slope of $m^2/t$ is used for the $\cos\Theta$ calculation.

$$c = \frac{m^2}{t}\,\frac{\eta}{\rho^2 \sigma \cos\Theta} \quad \text{The geometric constant "c" can be} \tag{4}$$

determined with a fluid of contact angle 0.

Usually, as done herein, n-heptan is used, which has a low surface tension.

For $m^2/t$ the initial slope is used.

Test Liquids Parameters used herein:
n-Heptan for geometric factor "c" @ 20° C. (also possible n-Hexan)
η=Liquid dynamic viscosity [mPa s]=0.409
ρ =Liquid density [g/cm³]=0.684
σ =Liquid surface tension [mN/m]=20.4
cos Θ=Liquid contact angle (assumed 1=>low surface tension)
Saline solution 0.9% @ 10 C
η=Liquid dynamic viscosity [mPa s]=1.328
ρ =Liquid density [g/cm³]=1.006
σ =Liquid surface tension [in N/m]=74.48
cos Θ =Liquid contact angle Measured via $\Delta m^2/\Delta t$ Test Protocol First, the geometric factor "c" is determined as follows.
Homogeneous n-Heptane is brought at a constant temperature of 20° C.

For each measurement (of a set of experiment, done to get an average value for one type of material) 2.8 g of the uncoated super absorbent polymers is weighed; equally, for each experiment, 2.8 g of the coated super absorbent material is weighed.

A steel mesh is put in each sample holder, so that it covers the wider holes of the holder of this equipment and the 2.8 g sample is placed in the holder.

The sample surface is made smooth without using additional pressure, e.g. the holder is tapped once slightly on table to smooth the sample surface. Namely, this has to be done such that the sample remains of the same porosity, e.g. that the density of the sample (($\rho\_{Sample}$) is 95%-105% of the bulk density of the material. The calipers of the single samples used to calculate an average herein should not deviate by more than 0.3 mm from the average over the samples.

The screw cap is closed and screwed down the piston. The caliper of the sample is recorded. The calipers ($h\_{Sample}$) of a single sample (used to calculate, together with other calipers, an average as described herein) should be such that the density of the sample inside the sample holder is 95-105% of the bulk density of the material. Density of the sample inside the sample holder ($\rho\_{Sample}$) can be calculated from the sample amount ($m\_{Sample}$, 2.8 g), the sample caliper ($h\_{Sample}$), and the sample area ($A\_{Sample}$, here 9.63 mm$^2$) according to:

$$\rho_{Sample} = \frac{m_{Sample}}{h_{Sample} \cdot A_{Sample}}$$

Then, the sample holder is inserted. The balance of the equipment is undone and test liquid n-Heptane is moved near to the sample and the sample holder.

Then, the measurement is started and the slope/curve of the (up-take in g)$^2$ vs. time in s=>($\Delta m^2/\Delta t$) is recorded.

A regression line is placed through the most linear part of the slope/curve.

This is repeated three times, with three fresh samples, prepared as above, to gain an average over four measurements.

Then, 'c' can be calculated according to formula above.

Then, the contact angle of the coated super absorbent material with saline solution 0.9% and the contact angle of the uncoated super absorbent polymer with saline solution 0.9% can be determined, as used herein.

The saline solution 0.9% is brought to a constant temperature of 10° C.

As above the samples are weighed and one by one, placed in the testing equipment.

Per sample, the slope/curve of the (up-take in g)$^2$ vs. time in s=>($\Delta m^2/\Delta t$) is recorded and a regression line is placed through the second and further data points (typically 3-6 points), e.g. typically the first data point is not used as it often deviates from the regression line, before up-take decreases (and absorption starts). This is repeated three times with fresh samples, to gain an average over four measurements.

The cos contact angle with saline solution 0.9% for each sample of the coated super absorbent material and the uncoated super absorbent polymers can then be obtained by formula 3 above and an average of the thus obtained cos Θ (theta) can be obtained, as used herein.

Surface Tension Reduction of Particulate Coated Super Absorbent Material as Useful Herein The surface tension of the coated super absorbent material herein and also of the super absorbent polymers prior to coating, as used herein can be determined via ASTM D1331 and EDANA ERT 150.

The method determines the surface tension of solutions of the coating agents (or other components), when washed off the coated super absorbent material or polymers. This test covers aqueous and non-aqueous solutions and also solutions in solvent mixtures.

For the measurement (at 23° C. and 50% humidity) a Kruess K10ST tensiometer can be used.

Each measurement is done as follows:

0.50 gram of the material to be tested is placed in a beaker.

40 ml of test liquid, a 0.9% saline solution, is placed in a 50 ml beaker (completely clean: no surfactant containing). The saline solution is based on EDANA ERT150: 9.0 gr NaCl in 1.0 l distilled, deionized water, whereof the surface tension should be more than 71 mN/m at 23° C. (to be checked before each test).

Then, the sample material is added to the 50 ml beaker with the solution and this is stirred for 3 minutes. Then, after another 2 minutes, the surface tension of the material-solution mixture is measured with the Wilhelmy plate method, as known in the art.

The test is repeated to get a duplicate and the average is calculated. If the difference between the two replicates is more than 1 mN/m, there is an error in the test and two new replicate test result need to be obtained, to calculate an average.

All documents cited in the Detailed Description of the Invention are, in relevant part, incorporated herein by reference; the citation of any document is not to be construed as an admission that it is prior are with respect to the present invention.

While particular embodiments of the present invention have been illustrated and described, it would be obvious to those skilled in the art that various other changes and modifications can be made without departing from the spirit and scope of the invention. It is intended to cover in the appended claims all such changes and modifications that are within the scope of the invention.

What is claimed is:

1. An absorbent article comprising an absorbent structure, said absorbent structure comprising a particulate super-absorbent material comprising a particulate core of super-absorbent polymers, said particulate core coated with a coating agent comprising an organic coating compound which has one or more polar groups, and wherein the coated particulate super-absorbent material has a contact angle and a corresponding cos $CA_m$, wherein the cos $CA_m$ is greater than 0.3 and has a specific surface area of at least 0.25 m$^2$ per gram, further wherein there is a gradient of coated super absorbent material within the total superabsorbent material of the absorbent structure, and wherein the absorbent structure comprises less than 10% by weight of absorbent fibers.

2. The absorbent article of claim 1 wherein said absorbent structure further comprises cellulose fibers.

3. The absorbent article of claim 1 wherein said absorbent article is selected from the group consisting of a sanitary napkin, a panty liner, a diaper, a training pant, and an adult incontinence article.

4. The absorbent article of claim 1 wherein the absorbent structure comprises less than 5% by weight of absorbent fibrous material.

5. The absorbent article of claim 1 wherein the absorbent structure comprises more than 50% by weight of super absorbent.

6. The absorbent article of claim 1 wherein the absorbent structure comprises a gradient of uncoated superabsorbent material.

* * * * *